(12) United States Patent
Tan et al.

(10) Patent No.: US 8,709,722 B2
(45) Date of Patent: Apr. 29, 2014

(54) METHODS FOR DETECTING DNA-BINDING PROTEINS

(75) Inventors: Yen Nee Tan, Singapore (SG); Xiaodi Su, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/573,142

(22) Filed: Aug. 24, 2012

(65) Prior Publication Data

US 2013/0052638 A1 Feb. 28, 2013

Related U.S. Application Data

(60) Provisional application No. 61/526,913, filed on Aug. 24, 2011.

(51) Int. Cl.
| | |
|---|---|
| *C12Q 1/68* | (2006.01) |
| *G01N 33/53* | (2006.01) |
| *C12M 1/34* | (2006.01) |
| *G01N 33/566* | (2006.01) |
| *C07H 21/02* | (2006.01) |
| *C07H 21/04* | (2006.01) |
| *C07H 19/04* | (2006.01) |

(52) U.S. Cl.
USPC .......... 435/6.1; 435/7.1; 435/287.2; 436/501; 536/23.1; 536/24.3; 536/26.6; 977/773; 977/902

(58) Field of Classification Search
USPC ........... 435/6.1, 7.1; 436/501; 536/23.1, 24.3, 536/26.6; 977/773, 902
See application file for complete search history.

(56) References Cited

U.S. PATENT DOCUMENTS

| | | | | |
|---|---|---|---|---|
| 5,830,655 | A * | 11/1998 | Monforte et al. | ............ 435/6.11 |
| 6,066,452 | A * | 5/2000 | Weissman et al. | ........... 435/6.11 |
| 2008/0311669 | A1 | 12/2008 | Mirkin et al. | |

OTHER PUBLICATIONS

Tan et al, Sensing of Transcription Factor through Controlled-Assembly of Metal Nanoparticles Modified with Segmented DNA Elements, 2010, ACS Nano, 4, 5101-5110.*
Tan et al, Sensing of Transcription Factor through Controlled-Assembly of Metal Nanoparticles Modified with Segmented DNA Elements, 2010, Supporting information, ACS Nano, 4, s1-s8.*
Loven et al, Interaction of estrogen receptors alpha and beta with estrogen response elements, 2011, Molecular and Cellular Endocrinology, 181,151-163.*
Su et al, Combinational Application of Surface Plasmon Resonance Spectroscopy and Quartz Crystal Microbalance for Studying Nuclear Hormone Receptor-Response Element Interactions, 2006, Anal. Chem., 78, 5552-5558.*
Xu et al., A gold-nanoparticle-based real-time colorimetric screening method for endonuclease activity and inhibition. Angew Chem Int Ed Engl. May 4, 2007;46(19):3468-70. Epub Mar. 27, 2007.
Search Report and Written Opinion issued Aug. 2, 2013 in corresponding SG Application No. 201206300-4.

* cited by examiner

*Primary Examiner* — Narayan Bhat
(74) *Attorney, Agent, or Firm* — Wolf, Greenfield & Sacks, P.C.

(57) ABSTRACT

There is provided a method for detecting binding of a DNA-binding protein to a target recognition sequence. The method comprises mixing in a reaction buffer a first set of metal nanoparticles, a second set of metal nanoparticles and a DNA-binding protein to form a mixture, and detecting the aggregation state of the mixture of metal nanoparticles. Each set of metal nanoparticles has a conjugated double-stranded DNA molecule having a single-stranded overhang at one end. The single-stranded overhangs of each set of DNA-conjugated metal nanoparticles are complementary to each other such that annealing of the complementary overhangs results in formation of the target recognition sequence that specifically binds the DNA-binding protein. The reaction buffer comprises an ionic species in a concentration sufficient to result in aggregation of the metal nanoparticles upon annealing of the first and second single-stranded overhang.

10 Claims, 6 Drawing Sheets
(5 of 6 Drawing Sheet(s) Filed in Color)

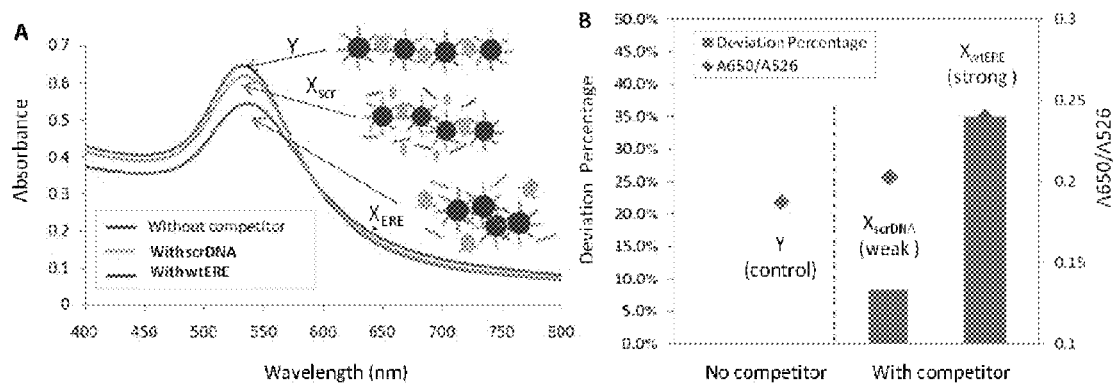

FIG. 9

| Name (denoted as) | Oligonucleotide Sequence | SEQ ID NO |
|---|---|---|
| Sense strand of consensus ERE (v) | 5'-GTCCAAAGTCA<u>GGTCA</u>CAGT<u>GACCT</u>GATCAAAGT-3' | 1 |
| (ds) ERE half site 1 (v1) | 5'-HS(CH$_2$)$_6$-GTCCAAAGTCA<u>GGTCA</u>CAG-3'<br>3'-CAGGTTTCAGT<u>CCAGT</u>-5' | 2<br>3 |
| (ds) ERE half site 2 (v2) | 5'-HS(CH$_2$)$_6$-ACTTTGATCA<u>GGTCA</u>CTG-3'<br>3'-TGAAACTAGT<u>CCAGT</u>-5' | 4<br>5 |
| Sense strand of scrambled DNA (s) | 5'-GTCCAAAGTCA<u>*ATCGC*</u>CAG<u>*CACGA*</u>TGATCAAAGT-3' | 6 |
| (ds) Scrambled half site 1 (s1) | 5'-HS(CH$_2$)$_6$-GTCCAAAGTCA<u>*ATCGC*</u>CAG-3'<br>3'-CAGGTTTCAGT<u>*TAGCC*</u>-5' | 7<br>8 |
| (ds) Scrambled half site 2 (s2) | 5'-HS(CH$_2$)$_6$-ACTTTGATCA<u>*TCGTG*</u>CTG-3'<br>3'-TGAAACTAGT<u>*AGCAC*</u>-5' | 9<br>10 |

FIG. 10

| Name (denoted as) | Oligonucleotide Sequence | SEQ ID NO |
|---|---|---|
| Sense strand of consensus ERE (v) | 5'-GTCCAAAGTCA<u>GGTCA</u>CAG<u>TGACC</u>TGATCAAAGT-3' | 1 |
| (ds) 45bp ERE half site 1 (v1_45bp) | 5'-HS(CH$_2$)$_6$-AAAAAGTCCAAAGTCA<u>GGTCA</u>CAG-3'<br>3'-TTTTTCAGGTTTCAGT<u>CCAGT</u>-5' | 11<br>12 |
| (ds) 45bp ERE half site 2 (v2_45bp) | 5'-HS(CH$_2$)$_6$-TTTTTTACTTTGATCA<u>GGTCA</u>CTG-3'<br>3'-AAAAAATGAAACTAGT<u>CCAGT</u>-5' | 13<br>14 |
| (ds) 25bp ERE half site 1 (v1_25bp) | 5'-HS(CH$_2$)$_6$-AAGTCA<u>GGTCA</u>CAG-3'<br>3'-TTCAGT<u>CCAGT</u>-5' | 15<br>16 |
| (ds) 25bp ERE half site 2 (v2_25bp) | 5'-HS(CH$_2$)$_6$-TGATCA<u>GGTCA</u>CTG-3'<br>3'-ACTAGT<u>CCAGT</u>-5' | 17<br>18 |
| (ds) 15bp ERE half site 1 (v1_15bp) | 5'-HS(CH$_2$)$_6$-AAGTCA<u>GGTCA</u>CAG-3'<br>3'-TTCAGT<u>CCAGT</u>-5' | 19<br>20 |
| (ds) 15bp ERE half site 2 (v2_15bp) | 5'-HS(CH$_2$)$_6$-A<u>GGTCA</u>CTG-3'<br>3'-T<u>CCAGT</u>-5' | |

FIG. 11

METHODS FOR DETECTING DNA-BINDING PROTEINS

CROSS-REFERENCE TO RELATED APPLICATION

This application claims benefit of, and priority from, U.S. provisional patent application No. 61/526,913 filed on Aug. 24, 2011, the contents of which are hereby incorporated herein by reference.

FIELD OF THE INVENTION

Aspects and embodiments of the invention relate to methods of detecting binding of a protein to double-stranded DNA.

BACKGROUND OF THE INVENTION

DNA-binding proteins are important biomolecules for life. Interactions of DNA-binding proteins with DNA at sequence-specific sites regulate gene expression during particular cellular events. Interactions between DNA-binding proteins and their target sequences in DNA are essential for many crucial cellular processes such as, for example, gene transcription, gene replication and gene recombination. DNA-binding proteins may be involved in regulation of various cellular mechanisms including, for example, control of cell cycle, cell death, cell response to various external signaling events, and cell metabolism.

The biological functions regulated by DNA-binding proteins (e.g., transcription factors) underlie their importance as biomarkers or targets for disease diagnosis and/or drug development. Thus, it is desirable to develop simple and robust methods for identifying DNA-binding proteins and to monitor their DNA-binding activities. Preferably, such identification methods would be amenable to high-throughput screening techniques.

To date, methods to detect DNA-binding proteins with sequence specificity such as, for example, fluorescent titration methods, gel shift assays, and DNA foot-printing assays are complicated, labor-intensive and time-consuming. The use of radioactive or fluorescent labels and specialized instruments/facilities in most of these techniques imposes limitations on cost, safety, usability and sensitivity for practical use. Such techniques are not adaptable to high-throughput formats, as often needed in biomedical research.

Metal nanoparticles (mNP) have unique optical properties which arise from their ability to support a localized surface plasmon resonance (LSPR). As a result of these unique optical properties, a solution of nanoparticles has a characteristic color, which can change depending on changes in the nanoparticles and/or the arrangement of the nanoparticles. Bioassays using nanoparticles have been developed for a wide range of analytes such as, for example, DNA, metal ions, and small molecules.

One straightforward method for mNP-based colorimetric assays involves functionalizing two sets of mNPs separately, each with probe and target biomolecules, and then directly detecting aggregation of the differently functionalized mNPs as a result of direct recognition between probe and target. This strategy is less than ideal for the design of protein-related assays because conjugation may change the conformation of a protein and affect the specific biomolecular interactions in which the protein is involved.

Many metal nanoparticles (mNP)-based colorimetric assays for DNA binding proteins are designed based on a crosslinking mechanism, in which two sets of mNP-conjugates are linked/assembled (in the presence of analyte) through permanent interparticle bond formation. This on-particle biorecognition process is slow and can take up to 12 hours to observe a color change. In addition, such analyte-induced aggregation mechanisms tend to produce false positive results caused by destabilizing effects of unrelated molecules that may be present in the reaction buffer, causing aggregation of the mNPs.

In contrast to a crosslinking mechanism, non-crosslinking mechanisms use unmodified mNPs that involve no inter-particle linkage and may provided relatively fast colorimetric response (within minutes). The stability of the mNPs is achieved via the controlled loss and/or gain of stabilization forces on the particle surface. For example, the addition of a salt to the reaction buffer may neutralize surface charges on the mNPs, causing the mNPs to aggregate. However, this type of assay is not suitable for use in protein sensing due to the largely available non-specific binding of proteins to the bare mNPs surface.

Other strategies involve the use of particle aggregates to detect a protein analyte that dissociates the aggregates into dispersed particles. A typical example is the endonuclease (DNase I) sensor for the detection of enzymatic cleavage activity and inhibition. This technology involves intensive inter-particle hybridization and requires careful monitoring of melting (dissociation) behavior of DNA. In addition, due to inaccessibility of DNA embedded inside the particle aggregates, this assay is limited in application, and is not useful for proteins that are large in size or which do not possess an enzymatic cleavage function.

SUMMARY OF THE INVENTION

Various aspects of the invention relate to a metal nanoparticle-based protein-DNA binding assay that is based, at least in part, on an elegant design of double-stranded DNA-metal nanoparticle (dsDNA-mNP) conjugates. A dsDNA-mNP conjugate is a metal nanoparticle conjugated at its surface to one end of a (e.g., one or more) double-stranded (ds) or partially dsDNA, the dsDNA containing at its other end a single-stranded (ss) DNA overhang (e.g., 3' or 5' end overhang). As used herein, an "overhang" may refer to one or more unpaired nucleotides in the end(s) of a dsDNA molecule. The end of the dsDNA containing the ssDNA overhang is not conjugated to the surface of a metal nanoparticle. The ssDNA overhang is free to bind to a complementary ssDNA overhang.

The assay uses two sets (e.g., two populations) of dsDNA-mNP conjugates. The dsDNA-mNP conjugates contain a "half site" segment of a functional dsDNA recognition sequence for a DNA-binding protein of interest. Each half site comprises a ssDNA overhang. The ssDNA overhangs of the dsDNA-mNP conjugates of the first set are complementary to the ssDNA overhangs of the dsDNA-mNP conjugates of the second set. Each ssDNA overhang may be about 2 to about 8 nucleotides in length. Under conditions that provide for annealing, the ssDNA overhangs of the dsDNA-mNP conjugates of the first set bind to the ssDNA overhangs of the dsDNA-mNP conjugates of the second set to form a double-stranded DNA molecule having a metal nanoparticle at each end (FIG. 1, center panel).

The ssDNA overhangs of the first set of dsDNA-mNP conjugates and the ssDNA overhangs of the second set of dsDNA-mNP conjugates, when annealed, form a double-stranded full-length target sequence that is recognized and bound by a DNA-binding protein of interest. In the absence of the DNA-binding protein and under appropriate ionic conditions such as, for example, appropriate concentrations of salt ions, annealing of the two ssDNA overhangs (each from a different set of dsDNA-mNP conjugates) can induce nanoparticle aggregation. In the presence of the DNA-binding protein, the nanoparticles do not tend to aggregate.

The methods provided herein are based, in part, on the observation that the combination of these two sets of dsDNA-mNP conjugates with complementary overhangs tend to aggregate, in the absence of DNA-binding protein, under conditions that provide for annealing of DNA sticky ends (e.g., 5' or 3' ssDNA overhangs) and that also provide for neutralization of charges that occur at the surface of the nanoparticles. Nanoparticle aggregation is modulated by the presence of the DNA-binding protein that is able to bind to (e.g., binds to) the transiently formed, full-length target recognition sequence. The binding of the protein to the target recognition site (e.g., sequence) in DNA is thought to act as a steric spacer between adjacent nanoparticles, separating the nanoparticles to a greater extent than compared to when the particles are aggregated. This difference in aggregation states results in a solution color change, which is readily detectable, for example by colorimetric methods.

This "light off" sensing strategy using the analyte DNA-binding protein as a stabilizer to prevent particle aggregation (and thus prevent color change of the solution) may avoid false positive results which are often seen in "light on" assays in which the analyte binding results in particle aggregation. These are discussed in more detail below.

Other known protein detection methods using metal nanoparticles may have long incubation periods, may provide false positive results, may involve multiple tedious steps or stringent assay conditions, or may have low specificity. The methods as described herein have been designed to provide for fast, simple and specific detection methods. These methods allow for combination of the specificity found in cross-linking approaches and the rapidity of noncross-linking methods into a single assay.

Furthermore, modulation of aggregation of the metal nanoparticles by the DNA-binding protein helps to avoid false positive signals that arise in other methods as a result of spontaneous aggregation.

Thus, in one aspect, the present invention provides methods for detecting binding of a DNA-binding protein to a target recognition site. The methods comprise mixing in a reaction buffer a first set of metal nanoparticles, a second set of metal nanoparticles, and a DNA-binding protein to form a mixture, and detecting the aggregation state of the mixture of metal nanoparticles: The first set of metal nanoparticles has a first double-stranded DNA molecule conjugated thereto, the first double-stranded DNA molecule having a first single-stranded overhang at one end, the second set of metal nanoparticles having a second double-stranded DNA molecule conjugated thereto. The second double-stranded DNA molecule has a second single-stranded overhang at one end, the second single-stranded overhang being complementary to the first single-stranded overhang such that annealing of the first and the second single-stranded overhang results in formation of the target recognition sequence that specifically binds the DNA-binding protein. The mixing thereby results in annealing of the first single-stranded overhang with the second single-stranded overhang. The reaction buffer comprises an ionic species in a concentration sufficient to result in aggregation of the metal nanoparticles upon annealing of the first and second single-stranded overhang.

The first set of metal nanoparticles and the second set of metal nanoparticles may comprise a noble metal or a noble metal alloy, including for example gold or silver, or an alloy thereof.

The first and second double-stranded DNA molecules may each be conjugated to the first and second set of metal nanoparticles respectively by a thioether linkage.

The ionic species may comprise KCl, NaCl, $CaCl_2$ or phosphate buffered saline.

The first single-stranded overhang and the second-single stranded overhang may each be from 2 to 8 nucleotides in length.

The DNA-binding protein may be a transcription factor, a protein involved in replication, or an enzyme.

Detecting may comprise one or more of microscopy techniques, dynamic light scattering techniques, visual observation of color, UV-vis absorption techniques, and localized surface plasmon resonance techniques.

The methods may further comprise pre-incubating the DNA-binding protein with a free double-stranded DNA molecule that comprises pre-incubating a competitor target recognition sequence prior to the mixing.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The tables and figures, which illustrate, by way of example only, embodiments of the present invention, are as follows.

UV-vis spectra of the stable v1-mNPs conjugates under the same buffer conditions (curve a) is shown as a reference.

Figure 8:
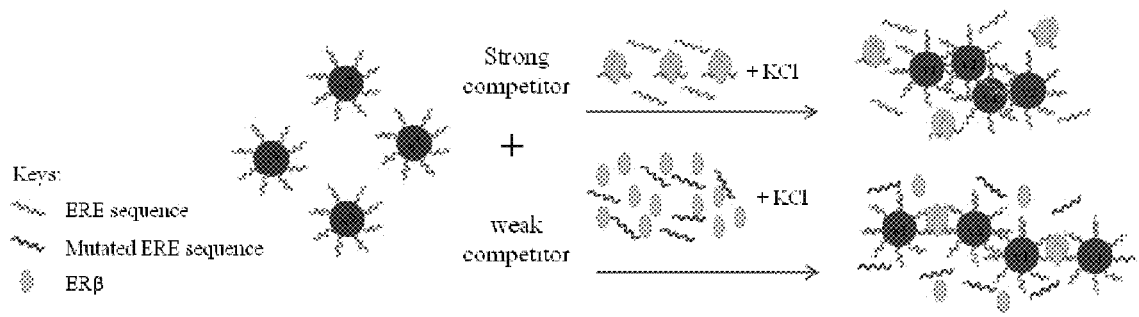

FIG. 8. Schematic illustration of competition assay for DNA-binding specificity study.

FIG. 9. A) UV-Vis spectrum showing the sequence specific competition assay. B) Aggregation degree (measured as A650/A526) and calculated deviation percentage ([(X−Y)/Y]*100%; X and Y denote samples with and without competitors, respectively).

FIG. 10. Lists the sequences of various oligonucleotides used in an exemplified embodiment of the methods of the invention.

FIG. 11. Lists the sequences of various oligonucleotides used in an exemplified embodiment of the methods of the invention.

DETAILED DESCRIPTION

In some aspects, the methods described herein include measuring sequence-specific interactions between DNA-binding proteins and target recognition sequences within double-stranded DNA. The methods are based, in part, on a novel design of double-stranded DNA segments having "sticky ends" (e.g., single-stranded overhang regions) that anneal to form a target recognition sequence. Some or all of the double-stranded DNA segments are each conjugated to a metal nanoparticle. The metal nanoparticles provide for colorimetric detection of protein binding to the target recognition sequence due to the surface plasmon resonant properties of the nanoparticles.

In some aspects, the methods described herein relate to the discovery that the DNA binding protein stabilizes self-assembled constructs of complementary dsDNA-metal nanoparticles (dsDNA-mNP) in solution under conditions where the complementary ends of the double-stranded DNA segments anneal and under ionic conditions where such annealing would otherwise promote aggregation of the metal nanoparticles to which the dsDNA segments are conjugated.

Figure 1:
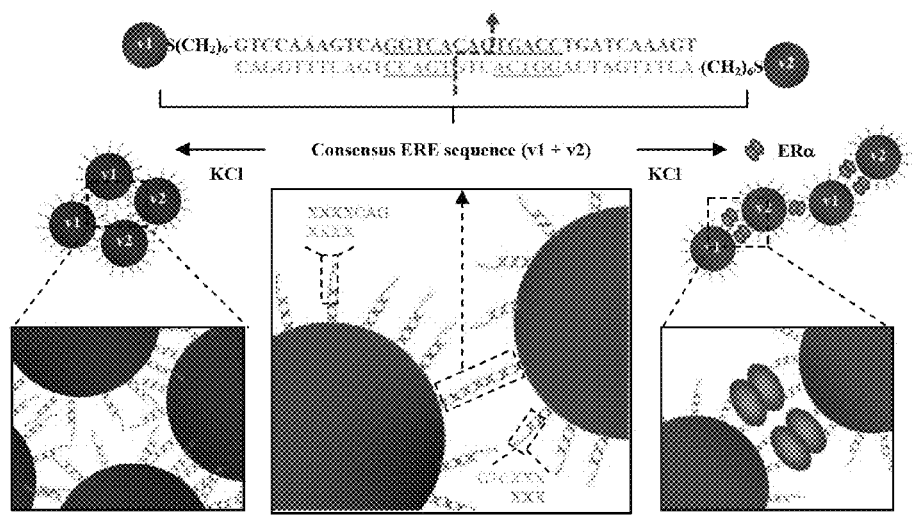
FIG. 1. Schematic illustration of an embodiment of the detection methods of the invention, using ERα and vit ERE as a model system. Sense strand of consensus ERE (v) (top sequence) (SEQ ID NO: 1); antisense strand of consensus ERE (v) (bottom sequence) (SEQ ID NO.

Without being limited to any particular theory, it appears that under annealing conditions that include ionic species in the annealing buffer, such as salt ions, and in the absence of DNA binding protein, base-pairing of the complementary overhang regions together with neutralization of surface charges on the nanoparticles by the ionic species in solution synergistically drive interactions between the metal nanoparticles to which the dsDNA segments are conjugated, as depicted in FIG. 1. The addition of the DNA binding protein to the system appears to result in binding of the protein to the full-length target recognition sequence that is formed by annealing of complementary dsDNA segments, the protein thus acting as a steric spacer between adjacent nanoparticles, thereby reducing the tendency of the particles to aggregate. This steric spacing appears to space the nanoparticles sufficiently apart to influence the resonance response of the particles, resulting in a color change as compared to the aggregated state. Thus, due to the surface plasmon resonant properties of the nanoparticles, solutions containing the nanoparticles will reflect different colors when the nanoparticles are in an aggregated state as compared to when the nanoparticles are sterically spaced by the stabilizing effect of the DNA binding protein.

Thus, in some embodiments, provided herein are methods of detecting a DNA-binding protein in a sample, including quantification or assessing the sequence specificity of the DNA-binding protein for a particular target recognition sequence.

As used herein, a protein in accordance with aspects of the invention may be referred to as a DNA-binding protein. The terms "protein" and "DNA-binding protein" may be used interchangeably and may refer to any protein that binds DNA. In some embodiments, the DNA-binding protein binds to double-stranded DNA in a sequence-specific manner, thus recognizing and binding to a specific sequence of nucleotides found within a double-stranded DNA molecule. The specific sequence to which the protein binds is referred to herein as a target recognition sequence or a target recognition site. The two terms may be used interchangeably. Many DNA-binding proteins and their particular consensus target recognition sequences are known. Examples of DNA-binding proteins include, without limitation, a transcription factors, including activators or suppressors of transcription, proteins involved in replication, or enzymes. The DNA-binding proteins bind dsDNA in a sequence-specific manner, and thus have a measurable binding affinity for target consensus sequences and may bind to sequences that have slightly altered sequences with a different (e.g., either greater or lesser) affinity.

In some embodiments, the methods comprise mixing (or combining or contacting) two sets (a first set and a second set) of metal nanoparticles and DNA-binding protein in a reaction buffer.

In the first set, the surface of the metal nanoparticles may be conjugated to a (e.g., one or more) double-stranded DNA (dsDNA) molecule containing at one end a ssDNA overhang, which comprises a portion of a target recognition sequence for the DNA-binding protein (referred to herein, in some instances, as a "first ds DNA molecule"). The end of the dsDNA that contains the ssDNA overhang is not conjugated to a metal nanoparticle.

In the second set, the surface of the metal nanoparticles may be conjugated to a (e.g., one or more) double-stranded DNA (dsDNA) molecule containing at one end a ssDNA overhang, which comprises a portion of a target recognition sequence for the DNA-binding protein (referred to herein, in some instances, as a "second ds DNA molecule"). The end of the dsDNA that contains the ssDNA overhang is not conjugated to a metal nanoparticle.

Thus, although the DNA molecule conjugated to a metal nanoparticle is described as "double-stranded", it will be appreciated that the DNA molecules are substantially double-stranded with a short single-stranded overhang region at one end, the end not conjugated to the nanoparticle. Such double-stranded DNA containing at one end a ssDNA may be referred to herein as partially double-stranded DNA.

In some embodiments, the sequences of the first and second dsDNA molecules are designed so that the single-stranded overhang of the first dsDNA molecule is complementary to and capable of annealing to (e.g., anneals to) the single-stranded overhang of the second dsDNA molecule, in order to form, at least transiently, one longer, entirely double-stranded DNA molecule. Further, the sequences of the first and second dsDNA molecules are designed so that when annealed, the longer formed DNA molecule contains an intact target recognition sequence that is available to be bound by (e.g., is bound by) any of the DNA-binding protein that may be present in a sample (or any DNA-binding protein).

In some embodiments, the single-stranded overhang portion (e.g., a ssDNA overhang) may be from 2 nucleotides in length to 8 nucleotides in length and, in some instances, may be 2, 3, 4, 5, 6, 7, 8, 9 or 8 nucleotides in length. The overhang may be a 3' overhang, meaning that the single-stranded overhang portion falls at the 3' end of the longer of the two strands that make up the dsDNA molecule (i.e. the "top strand" has the overhang). Alternatively, the overhang may be a 5' overhang, meaning that the single-stranded overhang portion falls at the 5' end of the longer of the two strands that make up the dsDNA molecule (i.e. the "bottom strand" has the overhang).

In some embodiments, the dsDNA molecules are designed such that the total length of the DNA molecule that is transiently formed by annealing of the two overhangs provides sufficient space for the DNA-binding protein to fit between adjacent, aggregated metal nanoparticles, while binding to the transiently formed target recognition site. For example, the full-length DNA molecule, once assembled, which will contain the assembled target recognition sequence, may be from 10 to 100 nucleotides. The precise length may depend on factors such as the type of nanoparticles (e.g., gold or silver), the length of the target recognition sequence, the size of the DNA-binding protein, and/or the manner in which the DNA-binding protein binds to the target recognition sequence. A skilled person can readily test a suitable length of DNA required for any given nanoparticle, target recognition sequence and DNA-binding protein, using routine laboratory methods, and as set out in the Examples provided herein.

As will be appreciated, metal nanoparticles have unique optical properties arising from their ability to support a localized surface plasmon resonance (LSPR). Free electrons in the metal nanoparticle interact with the oscillating electric fields of light, resulting in an oscillating electron charge in the nanoparticles that is in resonance with a visible light frequency. In some embodiments, the size, shape and material of the metal nanoparticle may influence the LSPR. Interparticle distance may also influence the LSPR and, thus, the color appearance of the solution containing the nanoparticles.

The metal nanoparticles used in accordance with the methods provided herein may be any metal nanoparticles that possess LSPR properties, including, without limitation, metal nanoparticles that comprise a noble metal, for example, silver or gold, or an alloy of such a metal. In some embodiments, the metal nanoparticles comprise gold, silver, a gold alloy, or a silver alloy. Nanoparticles are available with a variety of different nanostructures, and include, without limitation, gold nanorods, silver nanoplates and gold nanoplates.

In some embodiments, the metal nanoparticles used in each of the two sets of nanoparticles may be the same nanoparticles prior to conjugation of any DNA molecule. In some embodiments, different metal nanoparticles may be used for each of the two sets of nanoparticles. That is, the metal nanoparticles used in the first set may have a different size, may comprise a different metal, or may have a different nanostructure than the nanoparticles used in the second set.

In some embodiments, the metal nanoparticles may have dimensions in the nanometer range, for example in the range of 5 to 100 nm. In some embodiments, the nanoparticles may have a dimension (e.g., diameter) of 5, 10, 15, 25, 30, 35, 40, 45, 50, 55, 60, 65, 70, 75, 80, 85, 90, 95 or 100 nm. In some embodiments, the nanoparticles are less than about 100 nm in diameter. The size of the metal nanoparticles chosen may influence the length of the DNA molecules. That is, with increasing dimension of nanoparticles, the total length of the annealed full-length DNA containing the assembled target recognition sequence may need to increase, in order to provide sufficient space for the DNA-binding protein to fit between adjacent nanoparticles linked by annealed dsDNA molecules. A shorter length of the total assembled DNA once annealed may result in the nanoparticles sterically hindering the DNA-binding protein, preventing access to the assembled full-length target recognition sequence. Thus, typically, the larger the dimensions of the nanoparticles, the longer the total length of the assembled DNA may need to be. A skilled person can readily test a suitable length of DNA required for any given nanoparticle, using routine laboratory methods, and as set out in the Examples provided herein.

The metal nanoparticles provided herein are conjugated to a double-stranded (or partially double-stranded) DNA. The DNA may be conjugated to a nanoparticle by any method used to conjugate an organic molecule such as DNA to a metal. For example, free thiol groups react with metal, forming a bond between the metal surface and the sulphur atom. Thus, the dsDNA may be synthesized with an end group containing a free thiol on one end (e.g., the 5' end) of one strand of dsDNA molecule, using standard laboratory techniques. The DNA molecule with a free thiol may be conjugated to the metal nanoparticle for use in any of the methods provided herein, thereby forming a thioether linkage between the metal nanoparticle and the DNA molecule.

In some embodiments, the two sets of metal nanoparticles, the first set containing metal nanoparticles conjugated to a first dsDNA molecule and the second set containing metal nanoparticles conjugated to a second dsDNA molecule, are mixed (or combined or contacted) in a reaction buffer and under conditions designed to provide appropriate conditions to allow for the complementary overhang regions of the dsDNA molecules to anneal. Annealing conditions for short DNA sequences are well known, including appropriate pH, temperature and ionic strength conditions.

In some embodiments, the reaction buffer provides appropriate conditions (e.g., pH, ionic concentration and non-denaturing conditions) to provide for binding of the DNA-binding protein to the target recognition sequence formed by annealing of two complementary single-stranded overhangs.

In some embodiments, the reaction buffer contains an ionic species such as, for example, salt. Examples of salts include, without limitation, potassium chloride (KCl), sodium chloride (NaCl), and/or calcium chloride ($CaCl_2$). In some embodiments, the reaction buffer may comprises phosphate buffered saline (PBS). The ionic species may be selected to assist with the annealing conditions for the complementary overhang regions of the DNA molecules. In addition, the ionic species may be selected for its ability to neutralise at least partially the charge present on the surface of the metal nanoparticles, resulting in aggregation of the nanoparticles upon annealing.

In some embodiments, the reaction buffer comprises an effective amount of an ionic species sufficient to drive annealing of the overhang regions and concomitant aggregation of the nanoparticles. The ionic species may be, for example, any inorganic or organic salt. As will be appreciated, the precise identity and concentration of the ionic species selected for inclusion in the reaction buffer will depend on the nature of the nanoparticle used and the design of the DNA molecules and the complementary overhang regions. For example, different types of nanoparticles (e.g. gold versus silver) may have different lower limits for the concentration of ionic species in order to still aggregate upon annealing of the complementary overhang regions. Similarly, the same type of nanoparticle (e.g., gold) may have different lower limits for the concentration of ionic species, depending on the particular ionic species used and other buffer components (e.g., KCl versus PBS). In some embodiments, the ionic species used comprises KCl, NaCl, or $CaCl_2$ at a final concentration of 25 mM or greater in the reaction buffer.

It is this combination of annealing and charge neutralization that results in aggregation of the metal nanoparticles in the reaction buffer in the absence of DNA-binding protein. Metal nanoparticles conjugated with only one of the first or second nucleotide will not aggregate in solution, even in the presence of the ionic species in the solution. Annealing of the complementary overhang regions between the two sets of nanoparticles in the absence of sufficient concentration of ionic species may still result in aggregation of the nanoparticles, but any such aggregation will occur at a measurably slower rate than with concomitant charge neutralization.

Aggregation of metal nanoparticles influences the resonant frequencies of the nanoparticles, and thus results in a shift in the colorimetric properties of the nanoparticles. The aggregated state of the nanoparticles can be readily detected using, for example, one or more visualization methods, including colorimetric or uv/vis detection methods. For example, the aggregation state of the nanoparticles may be observed using microscopic examination or dynamic light scattering to determine whether the nanoparticles are clumped together or are evenly dispersed in the reaction buffer. More rapid detection may be achieved by observation of the color of the reaction buffer by visual inspection, measurement of uv-vis absorbance, or measurement of localized surface plasmon resonance.

In some embodiments, the aggregation of nanoparticles is controlled by the presence of any DNA-binding protein in the sample that is added to the reaction buffer.

In some embodiments, sample that may contain the DNA-binding protein may be added to the reaction buffer prior to, simultaneously with, or subsequently to the mixing together (or combining or contacting) of the two sets of metal nanoparticles. That is, the DNA-binding protein will not inhibit the annealing and aggregated if present during the mixing of the two sets of metal nanoparticles. The DNA-binding protein is capable of binding to (e.g., binds to) the full-length target recognition sequence if added after the metal nanoparticles have aggregated.

That is, when the mixture of the two sets of nanoparticles also contains a DNA-binding protein that is capable of recognizing and binding to the full-length target recognition sequence formed by annealing of the two dsDNA molecules, DNA-binding protein will bind to full-length target recognition sequences formed between nanoparticles, modulating the aggregation state. As indicated above, the DNA-binding protein may act as a steric spacer, resulting in a reduction of aggregation between nanoparticles, thus influencing the interparticle distance and as a result affecting the resonance parameters of the nanoparticles.

Thus, in some embodiments, when there is a detectable amount of DNA-binding protein present (e.g., the amount of protein is above the lower detection limit of the assay), the presence of the DNA-binding protein will have a detectable effect on the aggregation state of the nanoparticles. The nanoparticles will appear less aggregated or even monodispersed in the reaction as compared to the aggregation state in the absence of DNA-binding protein, when observed using for example microscopy techniques or dynamic light scattering techniques. Similarly, colorimetric measurement of the reaction buffer may also be affected by the presence of DNA-binding protein, and a change in color or a shift in UV-vis absorption or localized surface plasmon resonance, as compared to in the absence of DNA-binding protein, may be detected.

In some embodiments, the methods provided herein include detecting the aggregation state of the metal nanoparticles in order to determine whether any DNA-binding protein is present in the sample (and optionally how much), as described above, using visual, colorimetric or other methods to determine the interparticle distance (e.g., the state of aggregation or dispersion) of the nanoparticles in the reaction buffer. The results of such detection may be compared to the aggregated state of nanoparticles in the reaction buffer in the absence of DNA-binding protein.

The binding of the DNA-binding protein to the target recognition is a specific binding event, meaning that the binding is reversible, measurable and saturatable (also referred to as "specific binding" or as one of the DNA-binding protein or the DNA target recognition sequence "specifically binding" to the other). Thus, in some embodiments, the binding of the DNA-binding protein to the target recognition sequence may have a specific affinity constant that can be measured. In some embodiments, the concentration of DNA-binding protein in a sample may be determined using titration methods, in order to develop a binding curve. Similarly, in some embodiments, the affinity binding constant between the DNA-binding protein and the target recognition sequence may be measured if the titration is performed using known concentrations of DNA-binding protein and nanoparticles.

In some embodiments, the specific binding affinity of the DNA-binding protein for various different target recognition sequences may be assessed using the methods provided herein. In some embodiments, the methods may be designed as a competitive assay, for example between a consensus target recognition site formed by annealing of the dsDNA molecules conjugated to each of the two sets of nanoparticles and a competitor altered target recognition sequence that differs from the consensus sequence.

In some embodiments, a molar excess amount of the competitor DNA is mixed with the DNA-binding protein prior to addition of the DNA-binding protein to the reaction buffer. The competitor DNA comprises a free (i.e. unconjugated to a metal nanoparticle) double-stranded DNA molecule that contains the competitor target recognition site. If the competitor DNA is a strong competitor, the DNA-binding protein may bind predominantly to the free competitor DNA and will have a lesser or minimal effect in preventing aggregation of the two sets of metal nanoparticles upon annealing in the presence of an ionic species. If the competitor DNA is a weak competitor, more of the DNA-binding protein may bind to the annealed target recognition sequence formed between nanoparticles, thus modulating the aggregation of the metal nanoparticles. In this way, a high throughput screening assay may be designed to test the binding affinity of the DNA-binding protein to a variety of different DNA sequences, without the need to synthesize a large number of different sets of metal nanoparticles conjugated with complementary DNA molecules.

As will be appreciated, the design of the methods as described herein is general, and the methods may be used to detect, quantify or test the specific binding affinity of any DNA-binding protein that binds to double-stranded DNA in a sequence-specific manner. The sequences of the dsDNA molecules having complementary overhang regions can be readily synthesized to adapt the methods for the DNA-binding protein of interest.

In contrast to other known assay methods that detect analyte-induced particle aggregation ("light on" assays), the methods as described herein, in some embodiments, are protein stabilization approaches ("light-off" assay) and thus may reduce false positive results which are often caused by unrelated particle de-stabilizing effects.

In addition, in some embodiments, the synergistic combination of annealing and charge neutralization at the nanoparticle surface to induce aggregation of the metal nanoparticles, combined with the steric spacing affect of the DNA-binding protein to reduce aggregation, allows for a rapid detection method that may not require long incubation periods.

In addition to the above methods, kits or commercial packages are provided for performing the methods. The kits or commercial packages may comprise two sets of metal nanoparticles as described herein. Briefly, as described, each set contains metal nanoparticles with a surface conjugated to a double-stranded DNA molecule. The double-stranded DNA molecule conjugated to the metal nanoparticles comprises a portion of a target recognition sequence and also comprises a short single-stranded overhang region that is complementary to the overhang region of the double-stranded DNA molecule conjugated to the surface of the metal nanoparticles of the other set, such that when the complementary overhang regions anneal together, the two double-stranded DNA molecules form a full-length target recognition sequence that is available to be bound in the assay by a DNA-binding protein.

The kit or commercial package may further include a suitable reaction buffer as described herein.

In other aspects of the invention, provided herein are methods of detecting binding of a protein to a target recognition site. In some embodiments, the methods comprise contacting in an ionic reaction buffer a first population of metal nanoparticles, a second population of metal nanoparticles, and a protein that binds to the target recognition site, wherein the metal nanoparticles of the first population are conjugated to partially double-stranded DNA containing a first ssDNA overhang at one end, and the metal nanoparticles of the second population are conjugated to partially double-stranded DNA containing a second ssDNA overhang at one end that is complementary to the first single-stranded overhang of the partially double-stranded DNA of the first population; annealing the first single-stranded overhang of the partially double-stranded DNA of the first population to the second single-stranded overhang of the partially double stranded DNA of the second population, thereby forming the target recognition site; and detecting presence or absence of metal nanoparticle aggregation, wherein absence of aggregation indicates binding of the protein to the target recognition site.

As used herein, "ionic reaction buffer" may refer to reaction buffer that comprises an ionic species at a concentration sufficient for metal nanoparticle aggregation.

In some embodiments, the metal nanoparticles (e.g., nanostructured metal powders) of the first population and/or the nanoparticles of the second nanoparticles comprise a noble metal or a noble metal alloy. In some embodiments, the noble metal comprises (or is comprised of) gold or silver, or an alloy thereof.

In some embodiments, the metal nanoparticles and the partially double-stranded DNA of the first population are conjugated through a thioether linkage and/or the metal nanoparticles and the partially double-stranded DNA of the second population are conjugated through a thioether linkage.

In some embodiments, the ionic reaction buffer is or comprises potassium chloride (KCl), sodium chloride (NaCl), calcium chloride ($CaCl_2$) and/or phosphate buffered saline (PBS).

In some embodiments, the first single-stranded overhang of the partially double-stranded DNA of the first population and the second-single stranded overhang of the partially double-stranded DNA of the second population are each 2 to 8 nucleotides in length.

In some embodiments, the protein is a transcription factor, a protein involved in replication, or an enzyme.

In some embodiments, the methods further comprising detecting the presence or absence of metal nanoparticle aggregation using a microscopy technique, a dynamic light scattering technique, visual observation of color, an ultraviolet (UV)-vis absorption technique, a localized surface plasmon resonance technique, or a combination thereof.

In some embodiments, provided herein are compositions comprising a first population of metal nanoparticles and a second population of metal nanoparticles, wherein the metal nanoparticles of the first population are conjugated to partially double-stranded DNA containing a first ssDNA overhang at one end, and the metal nanoparticles of the second population are conjugated to partially double-stranded DNA containing a second ssDNA overhang at one end that is complementary to the first single-stranded overhang of the partially double-stranded DNA of the first population, and wherein the first single-stranded overhang of the partially double-stranded DNA of the first population is bound to the second single-stranded overhang of the partially double stranded DNA of the second population, thereby forming a target recognition site. In some embodiments, the composition further comprises a protein that binds to the target recognition site. In some embodiments, the composition further comprises an ionic reaction buffer.

In some embodiments, the metal nanoparticles (e.g., nanostructured metal powders) of the first population and/or the nanoparticles of the second nanoparticles comprise a noble metal or a noble metal alloy. In some embodiments, the noble metal comprises (or is comprised of) gold or silver, or an alloy thereof.

In some embodiments, the metal nanoparticles and the partially double-stranded DNA of the first population are conjugated through a thioether linkage and/or the metal nanoparticles and the partially double-stranded DNA of the second population are conjugated through a thioether linkage.

In some embodiments, the ionic reaction buffer is or comprises potassium chloride (KCl), sodium chloride (NaCl), calcium chloride ($CaCl_2$) and/or phosphate buffered saline (PBS).

In some embodiments, the first single-stranded overhang of the partially double-stranded DNA of the first population and the second-single stranded overhang of the partially double-stranded DNA of the second population are each 2 to 8 nucleotides in length.

In some embodiments, the protein is a transcription factor, a protein involved in replication, or an enzyme. The present methods are further exemplified by way of the following non-limiting examples.

EXAMPLES

A detection assay as described herein was demonstrated using estrogen receptor α as a model DNA-binding protein together with double-stranded DNA segments that form an estrogen response element conjugated to gold or silver NPs as the sensing platform. UV-vis spectroscopy, TEM, and dynamic light scattering (DLS) measurements were conducted to characterize the particle aggregation/dispersion mechanism.

Example 1

Design of dsDNA Conjugated AuNPs with Segmented DNA Elements

Estrogen receptor α (ERα), which binds specifically with its dsDNA response element from vitellogenin A2 gene (vit ERE) containing the core binding sequence of 5'-GGTCAnnn TGACC-3' (n: spacer nucleotide) (SEQ ID NO: 21), is used as a model in this study. FIG. 1 shows the basic principle underlying this assay.

FIG. 1. Schematic illustration of sensing principle. Each of two sets of gold nanoparticles (AuNPs) is modified with a half ERE segment (v1 and v2) containing sticky ends of 3 bases in length. These particles, when mixed together at 1:1 molar ratio, have a tendency to aggregate through Watson-Crick base-pairing force (middle). Addition of KCl neutralizes the charge repulsion between DNA-AuNPs and promotes base pairing between the complementary half ERE segments, resulting in rapid particle aggregation and solution color change from red to purple (left). In the presence of ERα, binding of the protein to the transient full ERE sequence between AuNPs exerts steric force to stabilize the AuNPs, preventing the extensive aggregation effect; thus the solution color remains or returns to red (right).

Table 1 sets out nucleotide sequences used in the ERE half sites and the scrambled half sites used as indicated in these Examples. The consensus vit dsERE (Table 1) was split into two half ERE segments (denoted as v1 and v2 respectively), each with a three base complementary sticky end. The half segments were conjugated onto AuNPs to form v1-AuNPs and v2-AuNPs conjugates, respectively. These as-prepared (unmixed) AuNPs conjugates (in 0.1 M PBS) were red in color and showed no traces of aggregation even in 25 mM KCl buffers (see TEM image in FIG. 2A). Noticeable particle aggregation was observed (FIG. 2B) when two sets of complementary v1-AuNPs and v2-AuNPs conjugates were mixed at 1:1 ratio under same buffer conditions. The LSPR peak of the AuNPs conjugates was shifted to a longer wavelength with band broadening (from curve a to b, FIG. 2C), accompanied by a visible solution color change from red to purple (insets of FIG. 2C).

To test this hypothesis, a control experiment was conducted using a mixture of dsDNA-AuNPs conjugates that carry non-complementary overhang ends, i.e., v1-AuNPs with s1-AuNPs (s1 is a half site of a non ERα binding DNA, in which the ERE site is scrambled. s1 has a non-complementary overhang end with v1 sequence. The sequences of the two half sites of scrambled DNA, i.e., s1 and s2, are shown in Table 1). The UV-vis spectrum of the v1-AuNPs and s1-AuNPs mixture (1:1 ratio) measured after 20 min of incubation in the 25 mM KCl-containing protein binding buffer overlapped with the stable v1-AuNPs conjugates alone under the same buffer condition (FIG. 3).

Figure 3:
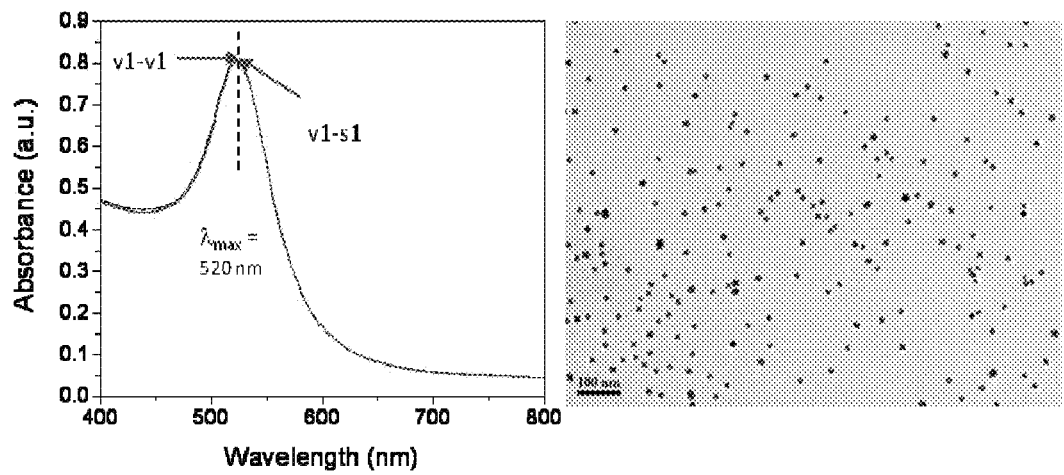
FIG. 3. UV-vis spectra (left) and TEM images (right) of non-complementary v1-s1 AuNPs mixture in the 25 mM KCl-containing protein binding buffer.

FIG. 3. UV-vis spectra (left) and TEM images (right) of non-complementary v1-s1 AuNPs mixture in the 25 mM KCl-containing protein binding buffer (0.1 M PBS, 25 mM KCl, 0.1 mM EDTA, 0.2 mM DTT and 1% of glycerol). The spectra and TEM images were taken after 20 min of incubation.

Based on the above-described results and discussion above, it is inferred that the hybridization tendency of the complementary nucleotides brings the particles into close proximity with each other, and the aggregation is driven at least in part by the presence of salt ions in the solution. As the melting temperature of the complementary nucleotides (-CAG-) used in this study is only 10° C., it is likely that the three DNA base pairs are not strong enough to stabilize the 34 bp full length vit ERE-AuNP structure for a significant period of time at room temperature. Furthermore, when the two particles are in close enough proximity, the charge screening effects by salt ions is amplified, leading to an observed extensive particle aggregation that increased as time elapsed.

TABLE I

| Name (denoted as) | Oligonucleotide Sequence | SEQ ID NO |
| --- | --- | --- |
| Sense strand of consensus ERE (v) | 5'-GTCCAAAGTCA<u>GGTCA</u>CAGT<u>GACC</u>TGATCAAAGT-3' | 1 |
| (ds) ERE half site 1 (v1) | 5'-HS(CH$_2$)$_6$-GTCCAAAGTCA<u>GGTCA</u>CAG-3'<br>3'-CAGGTTTCAGT<u>CCAGT</u>-5' | 2<br>3 |
| (ds) ERE half site 2 (v2) | 5'-HS(CH$_2$)$_6$-ACTTTGATCA<u>GGTCA</u>CTG-3'<br>3'-TGAAACTAGT<u>CCAGT</u>-5' | 4<br>5 |
| Sense strand of scrambled DNA (s) | 5'-GTCCAAAGTCA<u>ATCGC</u>CAG<u>CACGA</u>TGATCAAAGT-3' | 6 |
| (ds) Scrambled half site 1 (s1) | 5'-HS(CH$_2$)$_6$-GTCCAAAGTCA<u>ATCGC</u>CAG-3'<br>3'-CAGGTTTCAGT<u>TAGCC</u>-5' | 7<br>8 |
| (ds) Scrambled half site 2 (s2) | 5'-HS(CH$_2$)$_6$-ACTTTGATCA<u>TCGTG</u>CTG-3'<br>3'-TGAAACTAGT<u>AGCAC</u>-5' | 9<br>10 |

Figure 2:
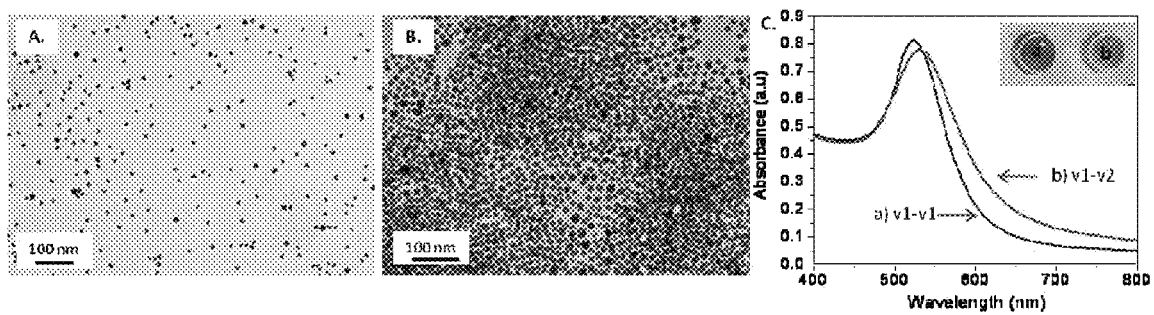
FIG. 2. TEM images of A) v1 AuNPs, and B) complementary mixture of v1-v2 AuNPs, each in a 25 mM KCl-containing protein binding buffer. C) UV-vis spectra of v1-AuNPs alone (curve a) and complementary v1-v2 AuNP mixture at 1:1 ratio (curve b).

FIG. 2. TEM images of A) v1 AuNPs and B) complementary mixture of v1-v2 AuNPs, in the 25 mM KCl-containing protein binding buffer (0.1 M PBS, 25 mM KCl, 0.1 mM EDTA, 0.2 mM DTT and 1% of glycerol). TEM samples were prepared by dispensing the dsDNA-AuNPs onto a copper grid after 20 min of reaction with salt buffer. C) UV-vis spectra of v1-AuNPs alone (curve a) and complementary v1-v2 AuNP mixture at 1:1 ratio (curve b) were taken at 1 min upon addition of salt buffer.

It was found that the complementary mixture of v1-AuNPs and v2-AuNPs also aggregated in buffer conditions without KCl after exposure to 0.1 M PBS for 20 min (data not shown). This observation indicates that the complementary sticky ends of the v1- and v2-sequences introduce base-pairing forces to facilitate nanoparticle aggregation, which is assisted by the presence of ions in solution.

Example 2

Length Effect of dsDNA-AuNPs Conjugates and Stability Test

To further understand the condition for the complementary conjugates to form aggregates, two shorter (15 and 25 bp) and one longer (45 bp) length of EREs were used to investigate the effect of the transient DNA length on aggregate formation.

Figure 4:
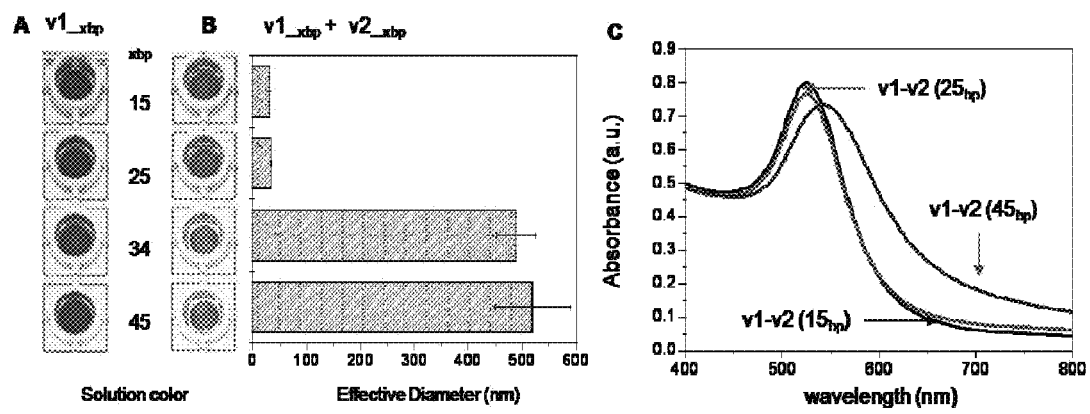
FIG. 4. Color photographs of A) v1_$_{xbp}$-AuNPs and B) (Left) complementary v1_$_{xbp}$-v2_$_{xbp}$ AuNP mixture in protein binding buffer. B) (Right) Aggregate size of particles (measured as effective hydrodynamic diameter by DLS) formed in the complementary mixture of AuNPs. C) UV-vis spectra of the complementary v1_$_{xbp}$-v2_$_{xbp}$ AuNPs.

Each of the EREs was split into two half segments with a complementary sticky end (see sequences in Table 2, and were conjugated onto AuNPs to form v1_$_{xbp}$-AuNPs and v2_$_{xbp}$-AuNPs (x=15, 25, 34, and 45), respectively. Dynamic light scattering (DLS) was used to measure the hydrodynamic diameter ($D_h$) of the particles. DLS results as shown in FIG. 4 revealed that large aggregates were formed only in the complementary mixture of AuNPs conjugates modified with the longer ERE segments of 34 bp ($D_h$=488.6±36.8 nm) and 45 bp ($D_h$=548.4±56.2 nm). For the complementary particle mixtures conjugated with shorter segments of EREs (15 and 25 bp), the $D_h$ (32.4±0.2 nm) remain similar to the v1-AuNPs alone (34.2±0.2 nm). The longer dsDNA-capping structures appear to promote base pairing between the sticky end sequences that are farther away from the particle interfaces, and thus lead to faster aggregation. The corresponding color change (from red to purple) for the 34 and 45 bp of DNA-AuNPs mixtures (left panel of FIG. 4B) and the LSPR spectra shift of these particles mixture (FIGS. 2C and 4C) correlate well with the DLS results, showing that the large aggregates have large hydrodynamic sizes, red shift spectra and darkened solution color.

confirms the distinctive stabilization effect of ERα throughout the tested period of 20 min. The same protein binding experiment was conducted for the AuNPs modified with the complementary half site of 45 bp ERE (v1_45 bp-v2_45 bp AuNPs). A similar stabilization effect was also observed in the presence of □ ERα (data not shown). It appears that the specific binding of ERα to its recognizable vit ERE sequence (formed through initial base-pairing between the complementary v1 and v2 half sites) may be responsible for the retainable stability of particle mixture, which would otherwise aggregate in the presence of the salt-containing buffer. The formation of v1-AuNPs/ERα/v2-AuNPs complex stabilizes the transient full ERE and inserts a sufficient steric barrier between the particles to prevent them from further aggregation.

TABLE 2

| Name (denoted as) | Oligonucleotide Sequence | SEQ ID NO |
|---|---|---|
| Sense strand of consensus ERE (v) | 5'-GTCCAAAGTCA<u>GGTCA</u>CAGT<u>GACC</u>TGATCAAAGT-3' | 1 |
| (ds) 45 bp ERE half site 1 (v1_45 bp) | 5'-HS(CH$_2$)$_6$-AAAAAGTCCAAAGTCA<u>GGTCA</u>CAG-3'<br>3'-TTTTTCAGGTTTCAGT<u>CCAGT</u>-5' | 11<br>12 |
| (ds) 45 bp ERE half site 2 (v2_45 bp) | 5'-HS(CH$_2$)$_6$-TTTTTTACTTTGATCA<u>GGTCA</u>CTG-3'<br>3'-AAAAAATGAAACTAGT<u>CCAGT</u>-5' | 13<br>14 |
| (ds) 25 bp ERE half site 1 (v1_25 bp) | 5'-HS(CH$_2$)$_6$-AAGTCA<u>GGTCA</u>CAG-3'<br>3'-TTCAGT<u>CCAGT</u>-5' | 15<br>16 |
| (ds) 25 bp ERE half site 2 (v2_25 bp) | 5'-HS(CH$_2$)$_6$-TGATCA<u>GGTCA</u>CTG-3'<br>3'-ACTAGT<u>CCAGT</u>-5' | 17<br>18 |
| (ds) 15 bp ERE half site 1 (v1_15 bp) | 5'-HS(CH$_2$)$_6$-AAGTCA<u>GGTCA</u>CAG-3'<br>3'-TTCAGT<u>CCAGT</u>-5' | 19<br>20 |
| (ds) 15 bp ERE half site 2 (v2_15 bp) | 5'-HS(CH$_2$)$_6$-A<u>GGTCA</u>CTG-3'<br>3'-T<u>CCAGT</u>-5' | |

FIG. 4. Length effects of dsDNA on AuNPs aggregate formation. Color photograph of A) v1_xbp-AuNPs and B) (Left) complementary v1_xbp-v2_xbp AuNPs mixture, in protein binding buffer containing 0.1 M PBS, 25 mM KCl, 0.1 mM EDTA, 0.2 mM DTT and 1% of glycerol. (Right) Aggregates size of particles (measured as effective hydrodynamic diameter by DLS) formed in the complementary mixture of AuNPs conjugates modified with different length of dsDNA (x=15, 25, 34 and 45 bp). DLS data and color photograph of the AuNPs were taken at 10 min upon addition of salt buffer. C) UV-vis spectra of the complementary v1_xbp-v2_xbp AuNPs taken at 1 min upon mixing in the 25 mM KCl-containing protein binding buffer.

Example 3

Protein Sensing Using Segmented dsDNA-AuNPs Conjugates

Using the 34 bp consensus ERE sequence as an example, the instability of the complementary mixture in KCl-containing PBS buffer was used to detect a sequence-specific protein binding event.

Figure 5:
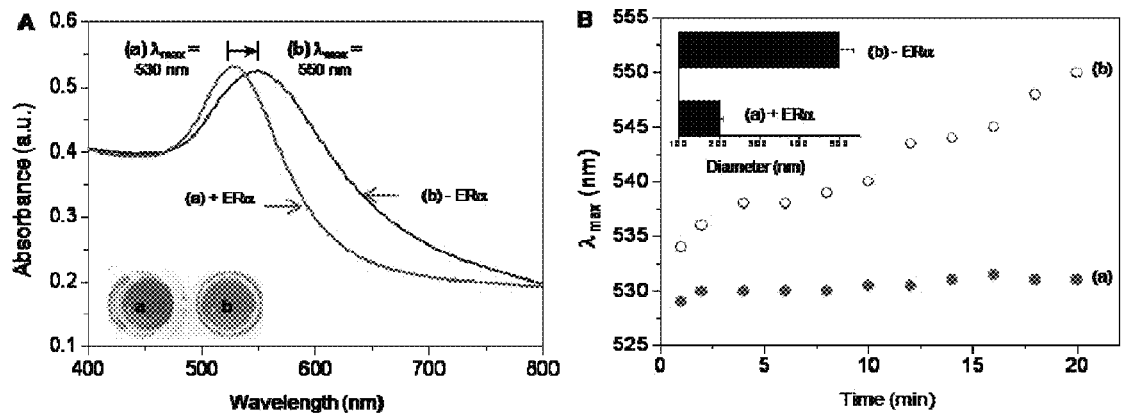
FIG. 5. (A) UV-vis spectra and (B) kinetic of LSPR peak ($\lambda_{max}$) shift of the complementary mixture of v1-v2 AuNPs (1:1 ratio) in the 25 mM KCl-containing protein binding buffer with ERα (curve a, solid sphere) and without ERα (curve b, hollow sphere). UV-vis spectra, color photographs (inset of A) and DLS data (inset of B) of the AuNPs.

Only a small shift in peak position ($\lambda_{max}$=530 nm) was observed in the complementary mixture of AuNPs conjugates when ERE-binding protein (i.e., ERα) was added (FIG. 5A). The time course of the particle aggregation (shown as a function of peak wavelength shift over time in FIG. 5B) for the mixture of v1-v2 AuNPs with (+) and without (−) ERα further FIG. 5. (A) UV-vis spectra and (B) kinetic of LSPR peak ($\lambda_{max}$) shift of the complementary mixture of v1-v2 AuNPs (1:1 ratio) in the 25 mM KCl-containing protein binding buffer with ERα (curve a, solid sphere) and without ERα (curve b, hollow sphere). UV-vis spectra, color photographs (inset of A) and DLS data (inset of B) of the AuNPs mixture were taken at 20 min upon addition of salt buffer.

Figure 6:
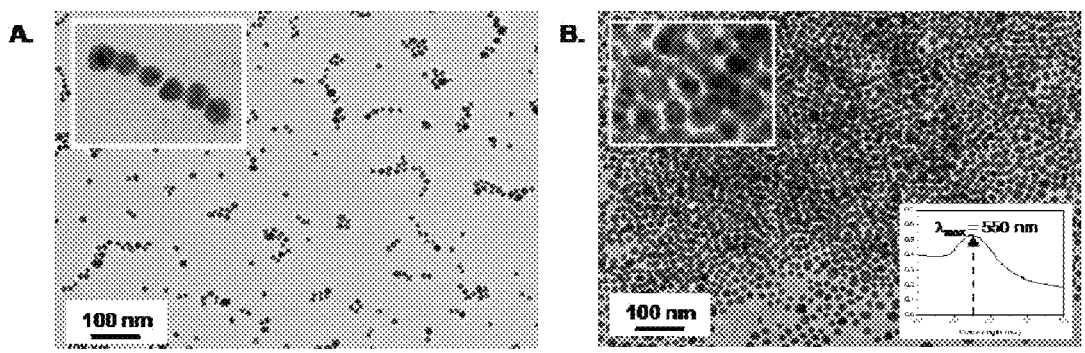
FIG. 6. TEM images of the complementary mixture of (A) v1-v2 AuNPs and (B) s1-s2 AuNPs in the presence of ERα.

To verify that the particle stabilization is due to the sequence-specific binding of ERα-ERE, experiments using a non-ERα binding scrambled DNA sequence as control were conducted. Two of the scrambled DNA half site, i.e., s1 and s2 (see sequences in Table 1) were functionalized on two sets of AuNPs respectively. The complementary scrambled dsDNA-AuNPs were then mixed together (1:1 molar ratio) and tested for stability in the presence of 100 nM of ERα. TEM images in FIG. 6 show that the complementary mixture of s1-s2 AuNPs (which can transiently anneal) underwent extensive aggregation, while the v1-v2 AuNP mixture shows no large aggregates formation but a few strands of short linear particle assemblies in the stable particle mixtures. These results show that the sequence-specific protein-DNA binding event is responsible for a higher stability of the complementary dsDNA-AuNPs mixtures using segmented protein binding sequences.

FIG. 6. TEM images of the complementary mixture of (A) v1-v2 AuNPs and (B) s1-s2 AuNPs in the presence of ERα (100 nM, final concentration), taken 20 min upon addition of 20 mM KCl buffer.

Example 4

Detection Sensitivity of Protein-DNA Binding Assay

In this experiment, the detection sensitivity of ERα binding to the complementary mixture of v1-v2 AuNPs was tested for a range of protein concentration (0 to 200 nM) in 50 mM KCl-containing buffer.

Figure 7:
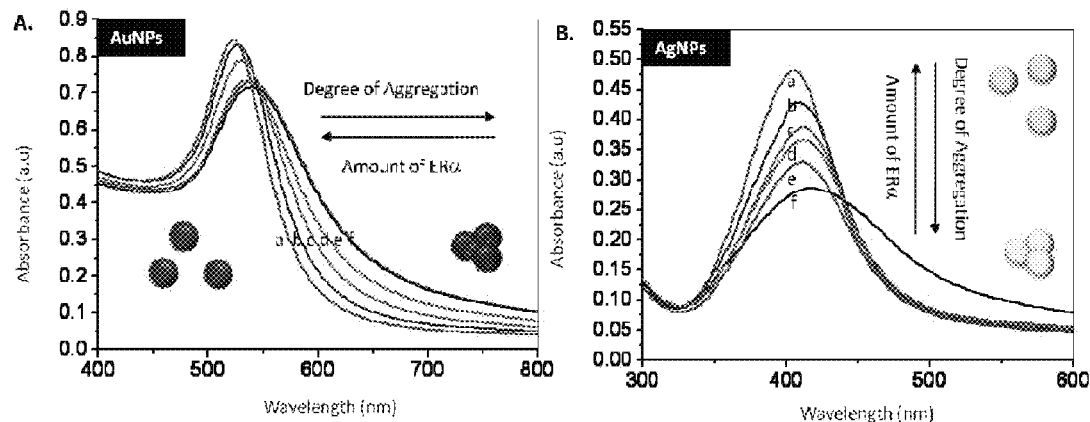
FIG. 7. UV-vis spectra of the complementary mixture of v1-v2 particles conjugates for (A) AuNPs and (B) AgNPs with b) 200 nM, c) 100 nM, d) 50 nM, e) 25 nM and f) 0 nM of ERα in 50 mM KCl-containing protein binding buffer.

FIG. 7A shows that ERα effectively retarded the aggregation of the complementary mixture of v1-v2 AuNPs. The degree of stabilization was increased with increasing protein concentration. For example, only a slight shift in the UV-vis spectrum was observed for the v1-v2 AuNP mixture in the presence of 200 nM ERα (the highest concentration tested) (curve b) relative to a stable v1-AuNP conjugate (curve a) at t=1 min. In such a short incubation time, ERα down to 50 nM can be detected by a noticeable stabilization effect. Both the improved ERα-ERE binding efficiency and the larger shift in LSPR peak (relative to a stable v1-AuNPs at $\lambda_{max\_v1}$=520 nm) for the v1-v2 AuNPs mixture in the 50 mM KCl-containing buffer (i.e., $\Delta max_{v1v2}$=545 nm, curve f in FIG. 7) are attributable to the effective detection of low concentration of ERα in a short incubation time. Indeed, when the comparison was made for the 1 min binding of 100 nM ERα in the 25 mM KCl—(FIG. 2C) and 50 mM KCl-containing buffer solutions, it was found that the recovery of the peak wavelength (i.e., $\Delta\lambda_{max}=\lambda_{max\_v1v2}-\lambda_{max\_v1v2-ER\alpha}$) for the former and latter conditions are 5 and 15 nm, respectively. These results suggest that the less stable the v1-v2 AuNP mixture is in (high) salt solution, the faster the aggregation will occur and the more readily stabilization effects of ERα can be detected in short assay time. The protein binding-particle stabilization mechanism used in this assay design also reduces the risk of obtaining false positive results caused by unrelated particle de-stabilizing effects.

FIG. 7. UV-vis spectra of the complementary mixture of v1-v2 particles conjugates for (A) AuNPs and (B) AgNPs with b) 200 nM, c) 100 nM, d) 50 nM, e) 25 nM and f) 0 nM of ERα in 50 mM KCl-containing protein binding buffer (0.1 M PBS, 50 mM KCl, 0.1 mM EDTA, 0.2 mM DTT and 1% of glycerol). UV-vis spectra of the stable v1-mNPs conjugates under the same buffer conditions (curve a) is shown as a reference. All the spectra were taken at 1 min upon addition of salt buffer.

In this study, segmented DNA-conjugated silver nanoparticles (AgNPs) were also prepared and tested for ERα binding to confirm the sensing strategy and to demonstrate the utility of AgNPs in this instance. The dsDNA-AgNP stability test shows that the mixture of the complementary v1-v2 AgNP conjugates (no ERα added) aggregated drastically in the 50 mM KCl-containing protein binding buffer solution (curve f, FIG. 7B). A noticeable dampening of the UV-vis spectra of AgNPs, particularly the drop in absorbance from its original peak wavelength of 400 nm (curve a, FIG. 7B) was observed, accompanied by an intense color change from yellow to pale brown. The binding of ERα (curve b-e, FIG. 7B), on the other hand, retarded the particle aggregation effectively in an ERα concentration-dependent manner. The detection limit of ERα binding using the AgNP assembly platform was found to be 25 nM, which is lower than that obtained using the AuNP sensing probe under the same buffer conditions (50 mM KCl) and assay time (t=1 min). Thus, AgNPs may, under certain conditions, provide a more sensitive platform for protein detection in these methods.

Example 5

Competition Assay for DNA-Binding Protein Sequence Selectivity Studies

The application of the controlled assembly of segmented DNA-AuNP conjugates for biosensing may be further developed into a competition assay format for fast screening of protein selectivity to various DNA sequence. In this assay, free ERE competitor dsDNA was added to compete with the transiently formed full-length EREs conjugated to the AuNPs for ERβ binding (see schematic diagram in FIG. 8).

In this study, excess unmodified DNA competitor (i.e., wtERE and scrDNA, are used as strong and weak competitors, respectively) was pre-incubated with the ERβ at room temperature for 20 minutes to allow for complex formation (molar ratio of ERβ:dsDNA is 1:4), followed by the addition to the complementary mixture of v1-v2-AuNPs in 56 mM KCl, with final ERβ concentration of 360 nM. In the presence of strong competitor (wtERE), limited amount of ERβ bound to the ERE anchored on the AuNPs surface, leading to extensive particle aggregation in salt solution. The opposite result was seen with the weak competitor that is unable to form a complex with ERβ in the incubation buffer. The unbound ERβ was thus available to bind with the dsERE-AuNP conjugates, leading to particle stabilization through protein binding event as observed in the direct binding assay (see Example 3).

FIG. 8. Schematic illustration of competition assay for DNA-binding protein sequence selectivity study. Unmodified DNA of different sequences can be used as competitor DNA to compete with the DNA-conjugated AuNPs for sequence-specific protein binding. The presence of a strong competitor will cause the aggregation of segmented dsDNA-AuNPs conjugates due to the lost of binding molecules to stabilize the transient DNA structure against charge screening by salt ions.

The aggregation state of the AuNPs was quantified using UV-Vis absorption spectrum as indicated by the shift of LSPR peak at 526 nm wavelength to a longer wavelength (e.g. 650 nm). The UV-Vis absorbance ratio at 650 nm to that at 526 nm, i.e., A650/A526 is indicative of the particle aggregation degree where a higher ratio is directly related to a larger extent of aggregation. In this study, the deviation percentage (i.e., [(X−Y)/Y]*100%) was calculated based on the difference in aggregation ratio of AuNP samples (measure as A650/A526) with competitors (denoted as X) relative to that without competitor (denoted as Y) at 5 minutes after mixing in the 56 mM KCl-containing protein binding buffer. A distinct difference in UV-Vis spectrum and aggregation degree is shown in FIG. 9. A 9.0% of deviation was recorded for the scrambled DNA sequence (scrDNA). This result shows that the weak competitor, i.e., scrDNA, is unable to form complex with ERβ efficiently, due to the sequence recognition of ERβ to the consensus ERE (see Table 1). Ideally, there should be no uptake of ERβ for complex formation with unmodified dsDNA, which eases the maximum stabilization effect. Here, the deviation of up to 9.0% observed reveals the non-specific binding of ERβ to the unrecognizable dsDNA present. On the other hand, AuNP sample with the wild type ERE sequence as competitor recorded a deviation as high as 35.0% from the maximum stabilization exerted by the 360 nM ERβ to the system (without competitor) in 56 mM KCl solution. This result shows a high uptake of ERβ to form a complex with the competitor wtERE sequence during the incubation step, causing a large percentage of ERβ to be unavailable for stabilization of the DNA conjugated AuNPs in salt buffer.

FIG. 9. A) UV-Vis spectrum showing the sequence specific competition assay. B) Aggregation degree (measured as A650/A526) and calculated deviation percentage ([(X−Y)/Y]*100%; X and Y denote samples with and without competitors, respectively) upon mixing in 56 mM KCl-containing protein binding buffer for 5 min.

The ERβ sequence specificity studies above demonstrates the potential of this transient DNA-linked AuNP assembly for high throughput screening of sequence selectivity of DNA-binding protein in a competition format. Tedious and time-consuming conjugation of AuNPs with each DNA sequence can be avoided via this competition assay, which allows fast and easy detection with the direct addition of unmodified DNA for sequence selectivity test.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for detecting binding of a DNA-binding protein to a consensus target recognition sequence in the presence of a competitor target recognition sequence, the method comprising:

incubating the DNA-binding protein with a molar excess of a free double-stranded DNA molecule that comprises the competitor target recognition sequence that differs from the consensus target recognition sequence, to form a pre-incubated DNA-binding protein;

mixing in a reaction buffer a first set of metal nanoparticles, a second set of metal nanoparticles and the pre-incubated DNA-binding protein to form a test mixture, said first set of metal nanoparticles having a first double-stranded DNA molecule conjugated thereto, said first double-stranded DNA molecule having a first single-stranded overhang at one end, said second set of metal nanoparticles having a second double-stranded DNA molecule conjugated thereto, said second double-stranded DNA molecule having a second single-stranded overhang at one end, said second single-stranded overhang being complementary to said first single-stranded overhang such that annealing of said first and said second single-stranded overhang results in formation of the consensus target recognition sequence that specifically binds the DNA-binding protein, thereby annealing said first single-stranded overhang with said second single-stranded overhang, said reaction buffer comprising an ionic species in a concentration sufficient to result in aggregation of the metal nanoparticles upon annealing of the first and second single-stranded overhang;

detecting the aggregation state of the test mixture of metal nanoparticles; and comparing the aggregation state of the test mixture with the aggregation state of a first control mixture of metal nanoparticles and the aggregation state of a second control mixture of metal nanoparticles, wherein the first control mixture is formed by mixing in the reaction buffer the first set of metal nanoparticles, the second set of metal nanoparticles and the DNA-binding protein that has not been incubated with the free double-stranded DNA molecule, and the second control mixture is formed by mixing in the reaction buffer the first set of metal nanoparticles, the second set of metal nanoparticles and the DNA-binding protein that has been incubated with a free double-stranded DNA molecule that is known not to specifically bind the DNA-binding protein, whereby a difference in aggregation state between the first control mixture and the test mixture that is greater than a difference in aggregation state between the first control mixture and the second control mixture is indicative of specific binding of the DNA-binding protein to the competitor target recognition sequence.

2. The method of claim 1, wherein the first set of metal nanoparticles and the second set of metal nanoparticles comprise a noble metal or a noble metal alloy.

3. The method of claim 2, wherein the noble metal comprises gold or silver.

4. The method of claim 1, wherein the first and second double-stranded DNA molecules are each conjugated to the first and second set of metal nanoparticles respectively by a thioether linkage.

5. The method of claim 1, wherein the reaction buffer comprises one or more ionic species selected from the group consisting of KCl, NaCl, $CaCl_2$ and a phosphate buffered saline.

6. The method of claim 1, wherein the first single-stranded overhang and the second-single stranded overhang are each from 2 to 8 nucleotides in length.

7. The method of claim 1, wherein the DNA-binding protein is a transcription factor, a protein involved in replication, or an enzyme.

8. The method of claim 1, wherein said detecting comprises one or more detection technique selected from the group consisting of a microscopy technique, a dynamic light scattering technique, a visual observation of color, a UV-vis absorption technique, and a localized surface plasmon resonance technique.

9. The method of claim 1, wherein: the first set of metal nanoparticles and the second set of metal nanoparticles comprise gold or silver, or an alloy thereof; the first and second double-stranded DNA molecules are each conjugated to the first and second set of metal nanoparticles respectively by a thioether linkage; the reaction buffer comprises one or more of KCl, NaCl, $CaCl_2$ and a phosphate buffered saline; the first single-stranded overhang and the second-single stranded overhang are each from 2 to 8 nucleotides in length; the DNA-binding protein is a transcription factor, a protein involved in replication, or an enzyme; and said detecting comprises one or more detection technique selected from the group consisting of a microscopy technique, a dynamic light scattering technique, a visual observation of color, a UV-vis absorption technique, and a localized surface plasmon resonance technique.

10. The method of claim 2, wherein the noble metal alloy comprises a gold alloy or a silver alloy.

* * * * *

UNITED STATES PATENT AND TRADEMARK OFFICE
CERTIFICATE OF CORRECTION

| | | |
|---|---|---|
| PATENT NO. | : 8,709,722 B2 | Page 1 of 1 |
| APPLICATION NO. | : 13/573142 | |
| DATED | : April 29, 2014 | |
| INVENTOR(S) | : Yen Nee Tan et al. | |

It is certified that error appears in the above-identified patent and that said Letters Patent is hereby corrected as shown below:

In the Specification:

Column 4, line 41, "(SEQ ID NO:" should read -- (SEQ ID NO: 22). --

Signed and Sealed this
Twenty-fourth Day of February, 2015

Michelle K. Lee
*Deputy Director of the United States Patent and Trademark Office*

SEQUENCE LISTING

```
<160> NUMBER OF SEQ ID NOS: 22

<210> SEQ ID NO 1
<211> LENGTH: 34
<212> TYPE: DNA
<213> ORGANISM: artificial sequence
<220> FEATURE:
<223> OTHER INFORMATION: synthetic oligonucleotide

<400> SEQUENCE: 1
gtccaaagtc aggtcacagt gacctgatca aagt                              34

<210> SEQ ID NO 2
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 2
gtccaaagtc aggtcacag                                               19

<210> SEQ ID NO 3
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 3
tgacctgact ttggac                                                  16

<210> SEQ ID NO 4
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 4
actttgatca ggtcactg                                                18
```

```
<210> SEQ ID NO 5
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 5
tgacctgatc aaagt                                                      15

<210> SEQ ID NO 6
<211> LENGTH: 34
<212> TYPE: DNA
<213> ORGANISM: artificial sequence
<220> FEATURE:
<223> OTHER INFORMATION: synthetic oligonucleotide

<400> SEQUENCE: 6
gtccaaagtc aatcgccagc acgatgatca aagt                                 34

<210> SEQ ID NO 7
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 7
gtccaaagtc aatcgccag                                                  19

<210> SEQ ID NO 8
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 8
ccgattgact ttggac                                                     16

<210> SEQ ID NO 9
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 9
actttgatca tcgtgctg                                                   18

<210> SEQ ID NO 10
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 10
cacgatgatc aaagt                                                      15

<210> SEQ ID NO 11
<211> LENGTH: 24
<212> TYPE: DNA
<213> ORGANISM: artificial sequence
<220> FEATURE:
<223> OTHER INFORMATION: synthetic oligonucleotide
```

```
<400> SEQUENCE: 11
aaaaagtcca aagtcaggtc acag                                          24

<210> SEQ ID NO 12
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 12
tgacctgact ttggactttt t                                             21

<210> SEQ ID NO 13
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 13 tttttactt tgatcaggtc actg                                           24

<210> SEQ ID NO 14
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 14
tgacctgatc aaagtaaaaa a                                             21

<210> SEQ ID NO 15
<211> LENGTH: 14
<212> TYPE: DNA
<213> ORGANISM: artificial sequence
<220> FEATURE:
<223> OTHER INFORMATION: synthetic oligonucleotide

<400> SEQUENCE: 15
aagtcaggtc acag                                                     14

<210> SEQ ID NO 16
<211> LENGTH: 11
<212> TYPE: DNA
<213> ORGANISM: artificial sequence
<220> FEATURE:
<223> OTHER INFORMATION: synthetic oligonucleotide

<400> SEQUENCE: 16
tgacctgact t                                                        11

<210> SEQ ID NO 17
<211> LENGTH: 14
<212> TYPE: DNA
<213> ORGANISM: artificial sequence
<220> FEATURE:
<223> OTHER INFORMATION: synthetic oligonucleotide

<400> SEQUENCE: 17
tgatcaggtc actg                                                     14

<210> SEQ ID NO 18
<211> LENGTH: 11
<212> TYPE: DNA
```

-continued

```
<213> ORGANISM: artificial sequence
<220> FEATURE:
<223> OTHER INFORMATION: synthetic oligonucleotide

<400> SEQUENCE: 18
tgacctgatc a                                                            11

<210> SEQ ID NO 19
<211> LENGTH: 14
<212> TYPE: DNA
<213> ORGANISM: artificial sequence
<220> FEATURE:
<223> OTHER INFORMATION: synthetic oligonucleotide

<400> SEQUENCE: 19
aagtcaggtc acag                                                         14

<210> SEQ ID NO 20
<211> LENGTH: 11
<212> TYPE: DNA
<213> ORGANISM: artificial sequence
<220> FEATURE:
<223> OTHER INFORMATION: synthetic oligonucleotide

<400> SEQUENCE: 20
tgacctgact t                                                            11

<210> SEQ ID NO 21
<211> LENGTH: 13
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (6)..(8)
<223> OTHER INFORMATION: n is a, c, g, or t

<400> SEQUENCE: 21
ggtcannntg acc                                                          13

<210> SEQ ID NO 22
<211> LENGTH: 34
<212> TYPE: DNA
<213> ORGANISM: artificial sequence
<220> FEATURE:
<223> OTHER INFORMATION: synthetic oligonucleotide

<400> SEQUENCE: 22
caggtttcag tccagtgtca ctggactagt ttca                                   34
```